(12) United States Patent
Squire et al.

(10) Patent No.: US 6,179,858 B1
(45) Date of Patent: Jan. 30, 2001

(54) STENT EXPANSION AND APPOSITION SENSING

(75) Inventors: James C. Squire, Everett; Campell Rogers, Westwood; Elazer R. Edelman, Brookline, all of MA (US)

(73) Assignee: Massachusetts Institute of Technology, Cambridge, MA (US)

(*) Notice: Under 35 U.S.C. 154(b), the term of this patent shall be extended for 0 days.

(21) Appl. No.: 09/227,555

(22) Filed: Jan. 8, 1999

Related U.S. Application Data

(60) Provisional application No. 60/085,098, filed on May 12, 1998.

(51) Int. Cl.[7] .......................... A61B 17/00; A61M 29/00
(52) U.S. Cl. .......................... 606/198; 606/194; 606/159; 623/1.11
(58) Field of Search ................... 606/1, 108, 159, 606/191, 192, 194, 198; 623/1, 12, 1.1, 1.11

(56) References Cited

U.S. PATENT DOCUMENTS

| | | |
|---|---|---|
| 356,056 | 1/1887 | Arnold . |
| 4,016,864 | 4/1977 | Sielaff et al. . |
| 4,265,249 | 5/1981 | Schindler et al. . |
| 4,895,560 * | 1/1990 | Papantonakos ............ 606/159 |
| 5,013,396 | 5/1991 | Wise et al. . |
| 5,112,347 * | 5/1992 | Taheri ...................... 606/159 |
| 5,113,868 | 5/1992 | Wise et al. . |
| 5,224,491 | 7/1993 | Mehra . |
| 5,287,861 | 2/1994 | Wilk . |
| 5,405,337 | 4/1995 | Maynard . |
| 5,431,628 | 7/1995 | Millar . |
| 5,439,446 | 8/1995 | Barry . |
| 5,535,752 | 7/1996 | Halperin et al. . |
| 5,564,434 | 10/1996 | Halperin et al. . |
| 5,588,432 | 12/1996 | Crowley . |
| 5,665,103 | 9/1997 | Lafontaine et al. . |
| 5,702,418 | 12/1997 | Ravenscroft . |

* cited by examiner

*Primary Examiner*—Michael Buiz
*Assistant Examiner*—William Lewis
(74) *Attorney, Agent, or Firm*—Samuels, Gauthier & Stevens, LLP

(57) ABSTRACT

An apposition sensing system including a stent; a catheter assembly to which the stent is coupled for deployment into a lumen; and a sensor positioned on the catheter assembly adjacent to an end of the stent. The sensor is adapted to provide an electrical parameter which is indicative of apposition of the end of the stent to the inner wall of the lumen. In one aspect of the invention, the sensor includes first and second pressure sensors positioned at proximal and distal portions of the catheter assembly adjacent to proximal and distal ends of the stent. A monitoring unit monitors pressure changes sensed by the sensors. In accordance with an alternative embodiment of the invention, there is provided an expansion sensing system including a stent having an electrically conductive region; an expandable insulating sleeve; a catheter assembly to which the stent is coupled for deployment into a lumen; and at least one electrode associated with the catheter assembly. The sleeve is positioned between the electrode and the conductive region, the electrode and conductive region being adapted to provide an electrical parameter which varies in correspondence with expansion of the stent. In one aspect of the invention, the sleeve positioned between the electrode and the conductive region define a variable capacitor. A monitoring unit monitors variations in capacitance between the electrode and conductive region which is directly proportional to the change in stent diameter.

12 Claims, 6 Drawing Sheets

Table: Prototype Results

| Balloon Pressure (atm) | Stent diameter (mm) | Capacitance (pF) |
|---|---|---|
| 0 | 2.1 | 5.9 |
| 0+ | 2.7 | 8.9 |
| 2 | 2.9 | 10.0 |
| 3 | 2.9 | 10.4 |
| 4 | 3.0 | 13.9 |

FIG. 4

STENT EXPANSION AND APPOSITION SENSING

PRIORITY INFORMATION

This application claims priority from provisional application Ser. No. 60/085,098 filed May 12, 1998, now abandoned.

BACKGROUND OF THE INVENTION

The invention relates to the field of stents and in particular to systems which can sense the expansion and apposition of a deployed stent.

An endoluminal stent is a tubular structure inserted into a collapsing, weakened, and/or occluded passageway (e.g., blood vessel or exocrine duct) where it is expanded and left as a permanent scaffold. The most common variety is the balloon-expandable endovascular stent for the coronary artery, of which an estimated 200,000 were implanted in U.S. patients in 1997.

There are two criteria that must be satisfied for a stent implantation to be considered successful. The stent must be expanded to some minimum diameter along its length, and it must be completely in contact with the vessel wall. These two issues are not equivalent, as the diameter of a diseased coronary artery typically changes dramatically over short distances and is typically not axisymmetric. A focal lesion, for example, may require the proximal and distal ends of the stent to be further expanded than the middle in order to achieve full apposition.

It is desirable to achieve a stent expansion-monitoring system as a clinical aid in assisting optimal stent emplacement, and as an alarm warning the operator of various types of failures. As previously discussed, one endpoint criterion of successful stent implantation is achievement of some minimal lumen diameter. Failure to achieve this diameter will not only result in inadequate blood perfusion (the fundamental reason for intervention), but also may result in a lower blood-vessel-to-stent surface area ratio. This has been associated with the primary failure mode of stents: the chronic hyperproliferative growth of smooth muscle cells called neointimal hyperplasia. This growth impinges on the lumen and reduces blood flow enough in approximately 30% of all stented patients to require further intervention within three months.

An overexpanded stent can similarly cause serious complications. Although aneurysms (burst vessels) are rarely caused while stenting, post-mortem histological findings indicate that deep vessel injury caused by overstretching is a common resultant of stenting. This deep injury is believed to be the primary cause of neointimal hyperplasia and stent failure. The problem is exacerbated by the potential for the most common stent designs to open unevenly, with one hemicylindrical side overexpanded and the other underexpanded, still giving a circular lumen while hyperextending one half of the artery and inflicting deep arterial injury.

One of the two criteria for successful stent deployment is full apposition of the stent against the vessel wall, since any regions of the stent that protrude into the lumen causes blood turbulence leading to acute thrombosis and arterial blockage. The desire to prevent this leads to the common practice of dilating the stent after it is initially expanded with a high-pressure balloon. This procedure intentionally overexpands the stent to ensure full apposition, but causes unnecessary injury to the vessel, leading to neointimal hyperplasia.

The focal nature of many vessel lesions compounds this problem, as the proximal and distal ends may not be apposed to the vessel wall at the time the middle of the stent has expanded sufficiently to restore patency. FIG. 1 is a simplified cross section of a partially deployed stent 100 in a vessel 102 narrowed by plaque 104. The stent has restored patency, but is not fully apposed against the vessel wall. There does not presently exist a time- and cost-efficient method or device that can determine whether the end struts of a stent are adequately apposed.

SUMMARY OF THE INVENTION

The invention is an improvement upon the design of a catheter assembly used to deploy balloon-expandable endoluminal stents. Specifically, it has been demonstrated how miniature capacitive sensors embedded into the catheter may be employed to inform the operator of the degree of circumferential expansion of the stent during and after its deployment (expansion-sensing), and when the stent's proximal and distal struts are in full contact with the interior lining of the vessel wall (apposition-sensing). This information is generated in real-time, three-dimensional, does not require x-ray exposure, and can be acquired with only minor modifications to presently available catheter designs.

The invention is inexpensive, requires no extra time to use, and can be constructed in versions that can provide either simple binary apposed/non-apposed information or can monitor the continuum of the stent ends' approach to apposition. Knowledge of the degree of apposition prevents the need to overexpand the stent with attendant risks of deep vessel injury. The invention may be constructed in such a manner to provide localized apposition data limited to a particular region of the proximal/distal edge of the stent, allowing the operator to selectively further dilate a particular side, and alerting the operator of suboptimal stent expansion patterns.

According to one embodiment of the invention, there is provided an apposition sensing system including a stent; a catheter assembly to which the stent is coupled for deployment into a lumen; and a sensor positioned on the catheter assembly adjacent to an end of the stent. The sensor is adapted to provide an electrical parameter which is indicative of apposition of the end of the stent to the inner wall of the lumen. In one aspect of the invention, the sensor includes first and second pressure sensors positioned at proximal and distal portions of the catheter assembly adjacent to proximal and distal ends of the stent. A monitoring unit monitors pressure changes sensed by the sensors.

In accordance with an alternative embodiment of the invention, there is provided an expansion sensing system including a stent having an electrically conductive region; an expandable insulating sleeve; a catheter assembly to which the stent is coupled for deployment into a lumen; and at least one electrode associated with the catheter assembly. The sleeve is positioned between the electrode and the conductive region, the electrode and conductive region being adapted to provide an electrical parameter which varies in correspondence with expansion of the stent. In one aspect of the invention, the sleeve positioned between the electrode and the conductive region define a variable capacitor. A monitoring unit monitors variations in capacitance between the electrode and conductive region which is directly proportional to the change in stent diameter.

These and other objects, features and advantages of the present invention will become apparent in light of the following detailed description of preferred embodiments thereof, as illustrated in the accompanying drawings.

BRIEF DESCRIPTION OF THE DRAWINGS

FIG. 4 is a table of experimental data indicating that the sensor of the invention has a capacitance which is responsive to the degree of stent expansion;

DETAILED DESCRIPTION OF THE INVENTION

Figure 1:
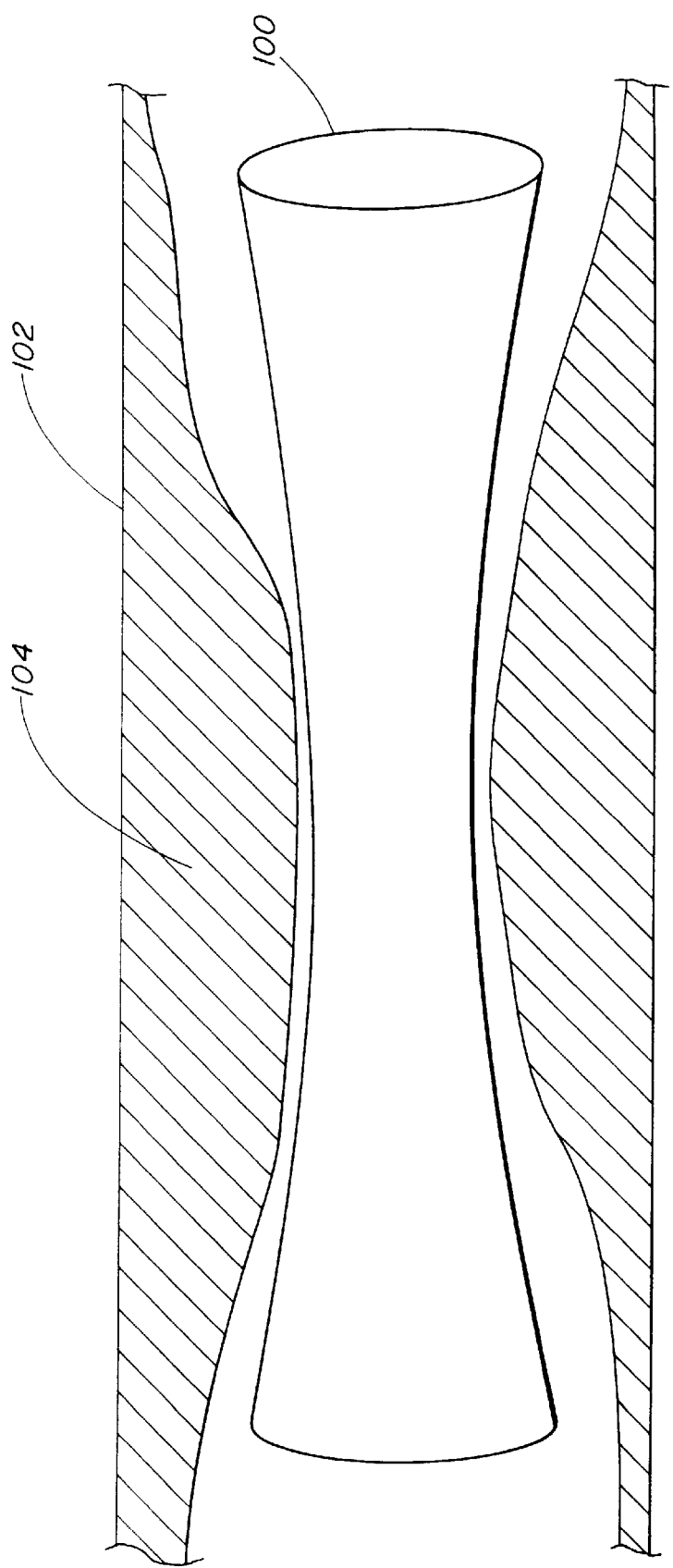
FIG. 1 is a simplified cross section of a partially deployed stent in a vessel narrowed by plaque.
Figure 2:
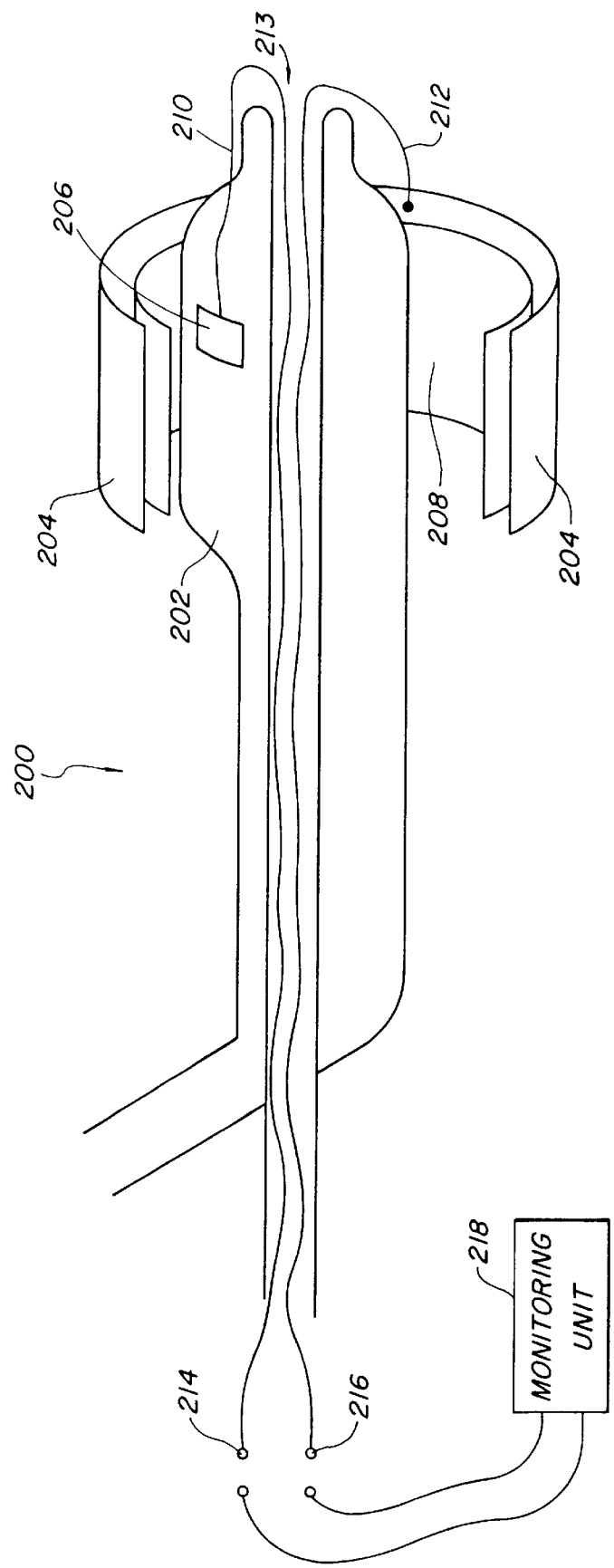
FIG. 2 is a simplified functional block diagram of a stent expansion sensing system in accordance with an exemplary embodiment of the invention.

FIG. 2 is a simplified functional block diagram of a stent expansion sensing system 200 in accordance with an exemplary embodiment of the invention. The system includes a balloon catheter 202 and a conductive stent 204. One or more conductive pads 206 are positioned on the balloon catheter in each region where independent expansion measurements are desired.

Over the conductive pad(s) is provided a thin, non-conductive expandable sleeve 208. The conductive stent is crimped onto the non-conductive sleeve, and wire conductors 210, 212 are connected to the pad and stent, respectively. The wires are fed through a guidewire lumen 213 to monitoring terminals 214, 216.

Alternatively, if a non-conductive stent is used, a second conductive pad may instead be connected to wire 210 and sandwiched between the insulating sleeve 208 and the stent, aligned directly over the first pad 206. The pad/sleeve/stent or pad/sleeve/pad combination forms a capacitor, which is monitored via terminals 214, 216. The change in capacitance is directly proportional to the change in stent diameter.

Endovascular stents are usually expanded in the coronary arteries under angiographic (x-ray) guidance. Since the stent itself is too thin to show clearly under angiography, radio-opaque dye is injected into the coronary artery to ascertain when the stent is fully deployed and the artery is patent. This approach yields an excellent sense of location of the catheter relative to the surrounding vasculature, and for that reason is always used during stenting procedures. It is also time efficient; the dye is injected through the same catheter used to perform predilation and stent deployment. The view obtained is a two-dimensional projection of the irregularly shaped lumen, which although adequate for maneuvering the stent into place can mislead the operator about the extent of stent expansion.

Figure 3A:
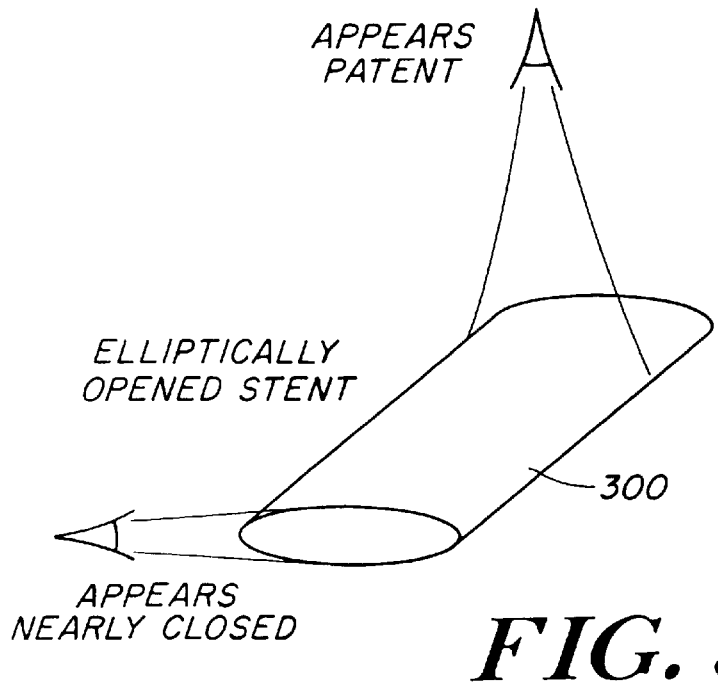
FIG. 3A is a depiction of an elliptically opened stent.
Figure 3B:
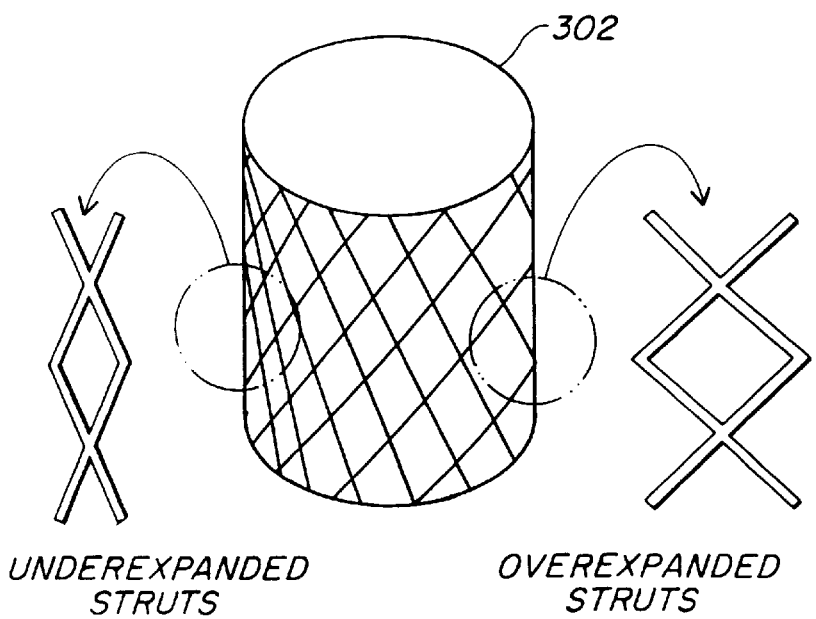
FIG. 3B is a depiction of a stent with portions which are underexpanded and over expanded.

Two common failure modes that occur during stenting can be identified by the expansion sensing system of the invention, but not by current methods and devices. With reference to FIG. 3A, angiography can only measure the projection of the three-dimensional arterial lumen on a two-dimensional plane. A partially opened stent 300 in an elliptically-shaped calcified lumen may appear fully dilated from one point of view when in fact adequate blood flow has not been restored. Referring to FIG. 3B, histology has shown a tendency of stents with circular cross-section to open unevenly, with one hemi-cylinder often over-expanded and the other underexpanded. Arterial sections subject to regional overexpansion are far more likely to experience complications from both acute thrombosis and chronic restenosis than evenly expanded sections.

An elliptically shaped region of plaque may resist stent dilation. Post-stenting angiography from one angle may lead the operator to conclude that blood flow has been fully restored when it has not. A catheter fitted with the expansion sensors of the invention would register that only certain regions were dilated, alerting the clinician to perform further anglographic examination.

Since most stents are not radio-opaque, the operator must infer the level of stent expansion from the perfusion of dye through the surrounding vasculature. This indirect method cannot warn of dangers such as the uneven hemi-cylindrical stent expansion shown in FIG. 3B. The manufacturers of the Johnson and Johnson slotted tube stent, the most commonly-used endovascular stent in the United States, have published data reporting this type of uneven angular expansion, which may greatly increase the patient's risk of acute and chronic complications. Angiography alone is not able to warn the clinician of this occurrence; the expansion-sensing balloon catheter can. Further, through partial reliance on the expansion-sensing catheter, the operator will need to inject less of the radio-opaque but unoxygenated dye into the patient's already ischemic coronaries, and subject the patient to a proportionally lower dosage of radiation.

Intravascular ultrasound (IVUS) can be used with confidence to gain a low-resolution view of the luminal cavity. It is the standard against which all other methods of estimating luminal diameter are measured and enables the operator to directly observe the degree and manner of stent expansion. Yet it is infrequently used during stenting procedures because of the long time required to repeatedly exchange the positions of the ultrasound probe and the balloon catheter, and the high cost of the disposable ultrasound tip. In contrast, the inexpensive expansion-sensing element of the invention is integrated into the balloon catheter and so its use incurs no time penalty.

As shown in FIG. 2, the basic sensing device of the invention is a capacitor formed by a conductive pad 206, an insulating sleeve 208 and the conductive stent 204. A prototype system has been constructed from a standard 3 mm angioplasty balloon catheter manufactured by Advanced Cardiovascular Systems (ACS). A 2 mm square of aluminum foil (10 $\mu$m thick) served as the conductive pad 206, to which was soldered a fine 40 gauge enameled wire that led through the central mechanical guidewire lumen 213. The foil pad was held in place by a compliant 60 $\mu$m thick sleeve of polyurethane (C-flex manufactured by ACS) that served as the capacitor's dielectric layer. A second 40 gauge enamel-insulated wire was threaded through the guidewire opening. The wire was sandwiched between the C-flex and the stent. Once the stent was crimped in place, the stent and wire made electrical contact. The foil pad/C-flex/stent formed a charge-storing capacitor, whose value was measured between terminals 214, 216 by monitoring unit 218. One may use any number of these capacitive sensors to gain expansion information around the perimeter and along the length of the stent body.

Theory predicts capacitance should be proportional to 1/t, where t is the thickness of the dielectric sleeve. This thickness in turn is a function of the stent radius, since the dielectric thins as it stretches. If a rough assumption is made that the dielectric attempts to maintain a constant volume and that the pressure it experiences is uniform, the rate it thins is proportional to 1/stent radial expansion and therefore the increase in capacitance is directly proportional to stent radial expansion. Experimental data, as shown in the table of FIG. 4, clearly indicate that the sensor's capacitance is responsive to the degree of stent expansion, in approximate agreement with theoretical predictions. The experiment was done in vitro with no artery to constrain the catheter, therefore the stent opened at a very low pressure designated in the table as 0+ atmospheres (atm). The capacitive sensor captured this moment of expansion accurately, an event that cannot be inferred through pressure monitoring. The capacitance at high pressures becomes nonlinear and increasingly sensitive to small increments in diameter. There were significant viscoelastic effects: at pressures 2 atm and higher the capacitance would slowly increase with time. This has been attributed to slow deformation of the dielectric.

Figure 5:
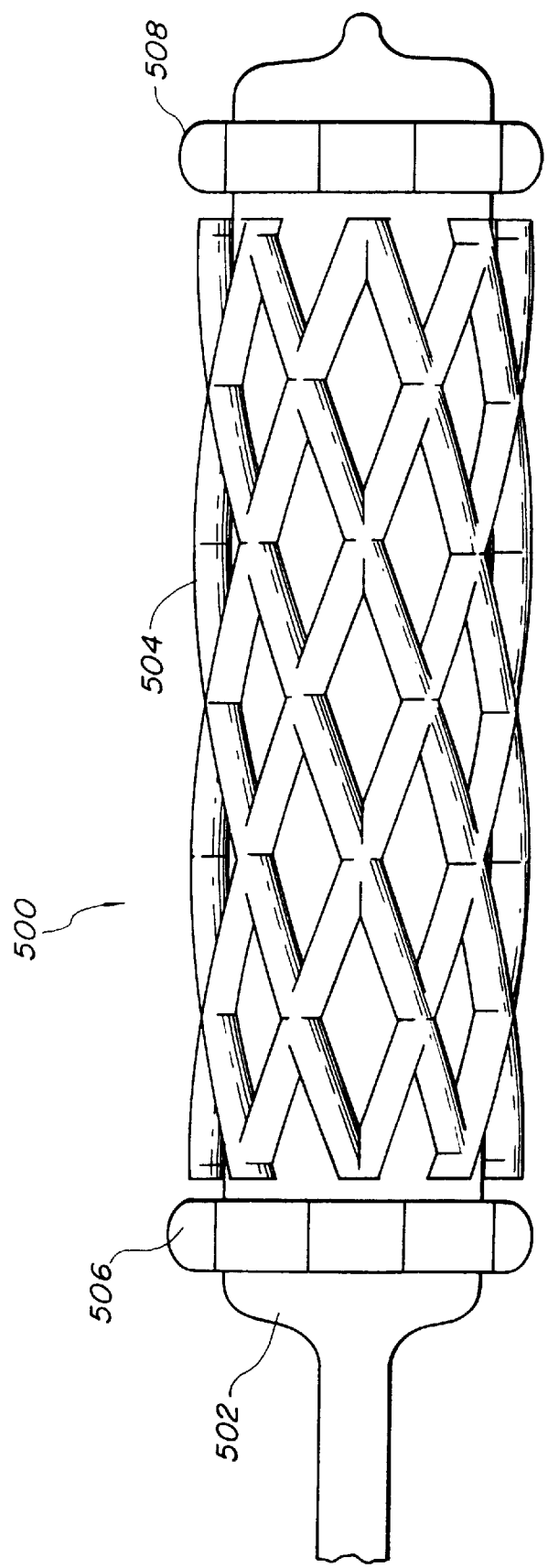
FIG. 5 is a simplified functional block diagram of a stent apposition sensing system in accordance with an exemplary embodiment of the invention.
Figure 6A:
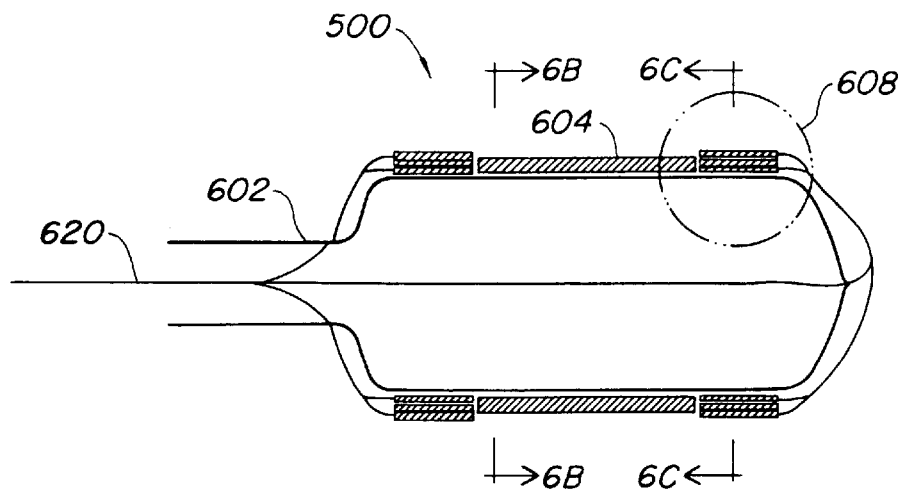
FIGS. 6A–6D are more detailed schematic block diagrams of the apposition sensing system shown in FIG. 5.
Figure 6B:
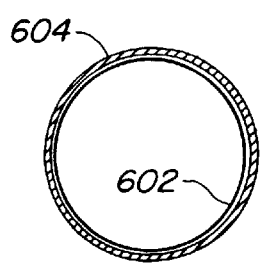
Figure 6C:
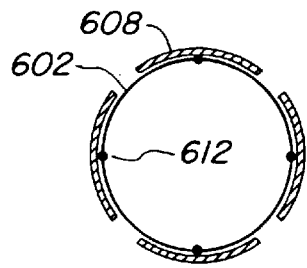
Figure 6D:
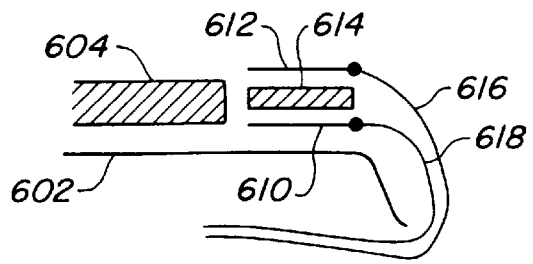

FIG. 5 is a simplified functional block diagram of a stent apposition sensing system 500 in accordance with an exemplary embodiment of the invention. The system includes a balloon catheter 502 and a conductive stent 504. A pair of annular arrays 506, 508 of capacitive compression sensors is mounted on the balloon catheter just proximal and distal to the stent. The arrays of sensors are slightly thicker than the stent, and therefore respond to arterial contact just prior to the stent.

FIGS. 6A–6D are more detailed schematic block diagrams of the apposition sensing system 500 shown in FIG. 5. The system consists of the two annular arrays 606, 608 of capacitive pressure sensors, mounted on the balloon 602 section of the catheter just proximal and distal to the conductive stent 604. Any stent-delivery catheter could be used for this purpose, such as the 3 mm compliant angioplasty catheter manufactured by Advanced Cardiovascular Systems. The arrays of capacitive sensors 608 consist of a conductive pad 610 attached to the balloon along the pad's centerline 612 permitting the pad's dimensions to remain unchanged as the balloon expands circumferentially. Both the interior pad 610 and an exterior conductive pad 612 can be fashioned from a 50 $\mu$m sheet of aluminum foil, cut to a 1 mm square. An easily-compressed (e.g., closed-cell polyurethane foam of 25 $\mu$m thickness) dielectric layer 614 separates the luminal (interior) pad 610 from the exterior pad 612. The capacitance between the pads is monitored via wires 616, 618, made from a material such as 40 gauge enamel-coated copper. The illustrated embodiment includes 4 proximal and 4 distal sensors, each which may share a luminal pad wire, for a total of 9 wires in a bundle 620 exiting the catheter base.

It has been experimentally shown that the exposed far proximal and distal ends of the balloon, unconstrained by the stent, expand circumferentially to make contact with the artery before the edges of the stent. Accordingly, an alternative embodiment of the invention uses 2 sets of 4 adjoining arrays of sensors, each of 1 mm width, mounted in a serial fashion along 4 mm of each side of the balloon to track the stent's approach to apposition.

There are currently two methods used to ensure stent strut apposition against the vessel wall: high-pressure post-dilation and, as previously described, inspection with intravascular ultrasound (IVUS). The former method uses a second high-pressure balloon, commonly inflated to 20 atmospheres of pressure, to further dilate the stent after the initial deployment (which is usually limited to approximately 8 atmospheres). This procedure usually ensures complete strut apposition. It has gained acceptance by most operators because it is fast (a single catheter exchange is involved), reliable (as measured by the low probability of acute complications), and inexpensive. Practioners have recently called this practice into question, citing the frequency of incompletely-expanded stents after high-pressure dilation, as measured by IVUS. The philosophy of being "better safe than sorry" embodied by automatic high-pressure inflation also runs counter to mounting evidence that overexpansion of the artery ruptures internal vascular structures which has been shown to lead to hyperplasia, the primary failure mode of stents today. Despite these drawbacks, modern clinical practice favors the high-pressure post-dilation approach to IVUS because of the high cost in time and money associated with IVUS as described previously.

In contrast to IVUS, which involves catheter exchanges, the inexpensive apposition-sensing element of the invention is integrated into the balloon catheter and so its use incurs no time penalty. The invention does not require the manufacture of miniature integrated electronics, and so can be produced for significantly less cost than an ultrasound probe. Further, the sensing device can guarantee strut apposition, which cannot be ensured through automatic high-pressure dilation procedures.

The primary focus of the illustrated embodiments of the invention relates in particular to the balloon-expandable endovascular stent, although the essential aspects of the invention, the ability to sense circumferential expansion and apposition force against the vessel wall, may also find use among other types of stents, in angioplasty catheters, and in other balloon catheter designs.

Although the present invention has been shown and described with respect to several preferred embodiments thereof, various changes, omissions and additions to the form and detail thereof, may be made therein, without departing from the spirit and scope of the invention.

What is claimed is:

1. A system comprising:
    an endoluminal device including an endovascular stent;
    a catheter assembly to which said device is coupled for deployment into a lumen; and
    a sensor positioned on said catheter assembly adjacent to an end of said endoluminal device, said sensor being mechanically coupled to said lumen and adapted to provide an electrical parameter which is indicative of apposition pressure of said end of said endoluminal device to the inner wall of said lumen.

2. The system of claim 1, wherein said catheter assembly comprises a balloon catheter.

3. An endoluminal device apposition sensing system comprising:
    an endoluminal device;
    a catheter assembly to which said endoluminal device is coupled for deployment into a lumen; and
    first and second pressure sensors positioned at proximal and distal portions of said catheter assembly adjacent to proximal and distal ends of said endoluminal device; and
    a monitoring unit which monitors pressure changes sensed by said sensors which is indicative of apposition of said proximal and distal ends of said endoluminal device to the inner wall of said lumen.

4. The system of claim 1, wherein said endoluminal device comprises an endovascular stent.

5. The system of claim wherein said catheter assembly comprises a balloon catheter.

6. A system comprising:
  an endoluminal device including an electrically conductive region;
  an expandable insulating sleeve;
  a catheter assembly to which said endoluminal device is coupled for deployment into a lumen; and
  at least one electrode associated with said catheter assembly, said expandable insulating sleeve being positioned between said electrode and said conductive region, said electrode and conductive region being adapted to provide an electrical parameter which varies in correspondence with expansion of said endoluminal device.

7. The system of claim 6, wherein said endoluminal device comprises an endovascular stent.

8. The system of claim 6, wherein said catheter assembly comprises a balloon catheter.

9. An endoluminal device expansion sensing system comprising:
  an endoluminal device including an electrically conductive region;
  an expandable insulating sleeve;
  a catheter assembly to which said endoluminal device is coupled for deployment into a lumen;
  at least one electrode associated with said catheter assembly, said expandable insulating sleeve being positioned between said at least one electrode and said conductive region so as to define a variable capacitor; and
  a monitoring unit which monitors variations in capacitance between said at least one electrode and conductive region which is directly proportional to the change in device diameter.

10. The system of claim 9, wherein said endoluminal device comprises an endovascular stent.

11. The system of claim 9, wherein said catheter assembly comprises a balloon catheter.

12. A method of sensing expansion of a stent within a lumen, said stent being coupled to a catheter assembly for deployment into said lumen, said method comprising:
  providing at least one electrode on said catheter assembly and an insulating sleeve between said electrode and an electrically conductive region associated with said stent; and
  monitoring changes in an electrical parameter associated with said electrode and said conductive region which varies in correspondence with expansion of said stent.

* * * * *